United States Patent
Kadambi (10) Patent No.: US 10,561,333 B2
(45) Date of Patent: Feb. 18, 2020

(54) PROCEDURE AND A PORTABLE APPARATUS FOR DIAGNOSIS OF SEIZURES

(71) Applicant: Mocxa, LLC, Longmont, CO (US)

(72) Inventor: Raja Aditya Kadambi, Bangalore (IN)

(73) Assignee: Mocxa Health Private Limited, Bangalore, Karnataka (IN)

( * ) Notice: Subject to any disclaimer, the term of this patent is extended or adjusted under 35 U.S.C. 154(b) by 374 days.

(21) Appl. No.: 15/609,060

(22) Filed: May 31, 2017

(65) Prior Publication Data
US 2017/0354341 A1 Dec. 14, 2017

(30) Foreign Application Priority Data
Jun. 10, 2016 (IN) .............................. 201641019908

(51) Int. Cl.
| | | |
|---|---|---|
| A61B 5/04 | (2006.01) | |
| A61B 5/00 | (2006.01) | |
| A61B 5/0476 | (2006.01) | |
| H04N 5/76 | (2006.01) | |
| G16H 50/50 | (2018.01) | |
| A61B 5/048 | (2006.01) | |

(Continued)

(52) U.S. Cl.
CPC .......... *A61B 5/0476* (2013.01); *A61B 5/4094* (2013.01); *A61B 5/6803* (2013.01); *G16H 50/50* (2018.01); *H04N 5/76* (2013.01); *A61B 5/002* (2013.01); *A61B 5/0046* (2013.01); *A61B 5/048* (2013.01); *G16H 50/20* (2018.01); *H04N 5/782* (2013.01)

(58) Field of Classification Search
None
See application file for complete search history.

(56) References Cited

U.S. PATENT DOCUMENTS

| | | | | |
|---|---|---|---|---|
| 8,214,453 | B2 | 7/2012 | Estes | |
| 2004/0206862 | A1* | 10/2004 | Adelman | ............ A61M 5/1414 248/171 |

(Continued)

FOREIGN PATENT DOCUMENTS

| | | |
|---|---|---|
| CN | 203776901 U | 8/2014 |
| WO | 2005098726 A2 | 10/2005 |

OTHER PUBLICATIONS

Liu et al. Patient Tracking for Video/EEG Monitoring Based on Change Detection in DCT Domain (2005).*

*Primary Examiner* — Etsub D Berhanu
(74) *Attorney, Agent, or Firm* — James A. Sheridan; Sheridan Law, LLC (57) ABSTRACT

There are disclosed systems and methods for seizure diagnosis by video electroencephalography (Video-EEG). There is disclosed a fully automated, portable, point-of-care diagnostic video EEG device. In an embodiment, the device includes a tracker configured for placement on a patient. The tracker has a set of sensors disposed thereon. An EEG headset is configured for detecting electrical activities of a brain of the patient. The EEG headset is configured for communicating the electrical activities of the brain of the patient. A telescoping stand provides built-in sensors. A mobile computing device is in communication with the built-in sensors and in communication with the EEG headset. A set of wheels provides controlled movement of the telescoping stand. Other embodiments are also disclosed.

8 Claims, 8 Drawing Sheets

(51) Int. Cl.
  *H04N 5/782*   (2006.01)
  *G16H 50/20*   (2018.01)

(56) References Cited

U.S. PATENT DOCUMENTS

| | | | |
|---|---|---|---|
| 2006/0110049 A1* | 5/2006 | Liang | G06K 9/00362 |
| | | | 382/224 |
| 2006/0111644 A1* | 5/2006 | Guttag | A61B 5/048 |
| | | | 600/544 |
| 2008/0021341 A1* | 1/2008 | Harris | A61B 5/0031 |
| | | | 600/544 |
| 2008/0045807 A1* | 2/2008 | Psota | A61B 5/0059 |
| | | | 600/300 |
| 2015/0157252 A1* | 6/2015 | Sabesan | A61B 5/4094 |
| | | | 600/301 |
| 2015/0223731 A1* | 8/2015 | Sahin | A61B 5/16 |
| | | | 600/301 |
| 2015/0335294 A1* | 11/2015 | Witcher | A61B 5/4094 |
| | | | 600/383 |

\* cited by examiner

DIAGRAM FOR PRIOR ART VIDEO EEG APPARATUS

DATA FLOWCHART

FIG. 3

EEG HEADSET + TRACKER

PROCEDURE AND A PORTABLE APPARATUS FOR DIAGNOSIS OF SEIZURES

REFERENCE TO PENDING PRIOR PATENT APPLICATION

This application claims the benefit of India Provisional Patent Application Number 201641019908, filed Jun. 10, 2016, by Raja Aditya Kadambi for "AN IMPROVED PROCEDURE AND A PORTABLE APPARATUS FOR DIAGNOSIS OF SEIZURES". This patent application is hereby incorporated herein by reference.

BACKGROUND

Seizures of various kinds, epileptic or otherwise, are neurological disorders that can be severely debilitating and/or dangerous to the individual and/or others. Epilepsy is characterized by the occurrence of seizures, in particular episodic impairment, loss of consciousness, abnormal motor phenomena, psychic or sensory disturbances. Research has found that its prevalence is high worldwide, particularly in less economically developed nations, suggesting that epilepsy sufferers may be in excess of one hundred million, worldwide.

An electroencephalogram (EEG) test is used for detecting abnormalities related to electrical activities of the brain. An EEG tracks and records brain wave patterns. In this procedure, conventionally, small metal discs with thin wires (electrodes) are placed on the scalp, wherein these wires from the electrodes are connected to the electroencephalograph (EEG) machine which then sends signals to a computer to process and record the results. The EEG machine detects and amplifies the electrical signals and records them onto a paper or computer. The test takes about an hour to a day. The electrodes are removed at the end of the test. This procedure is typically conducted in a healthcare facility or a diagnostic laboratory.

Video EEG test records the electrical activity of the brain on an EEG and simultaneously records a video of the physical manifestation of the seizure activity of the individual. The neurologist reads the EEG chart and views the video of the seizure to determine the nature of the seizure and come to a diagnosis. Research has proven beyond doubt that video EEG is a better diagnostic tool compared to traditional EEG.

Video EEG tests may be done at home or in a hospital setting. Video EEG monitoring duration ranges from a few hours to a week. Multiple sessions may often be required to reach the best diagnosis. Continuous monitoring is effective in cases where there are frequent seizures or the seizure activity can be triggered in a diagnostic setting, for example, by using flashing lights. An event button is activated by the subject, technologist or caregiver to mark the start and end of the seizure event(s).

In a typical procedure, the individual is placed in a room with the epilepsy monitoring unit with facilities for EEG, audio and video recording. The operator attaches several small patches (electrodes) to the subject's scalp. Wires from the electrodes are connected to the electroencephalograph (EEG) machine. The machine detects and amplifies the electrical signals and records them onto a paper or computer.

Increasingly, wireless systems are being used in monitoring rooms and few of the existing arts have been enumerated below.

U.S. Pat. No. 8,214,453 B2 discloses multiple cameras and microphones to be used in a home setting that are examined from various locations in the form of a home for long term ambulatory EEG monitoring. Video EEG monitoring with multiple cameras and microphones is no longer limited to a cabled hospital type setting. This device could also be utilized by hospitals to conduct video monitoring from any hospital type room.

CN 203776901 U discloses a electroencephalograph including a movable control console on a machine body, universal rotation shafts, rubber wheels, a computer comprising of a mouse, a keyboard and a computer table. This video electroencephalograph is simple in structure and convenient to use, time-saving and labor-saving in brain wave acquisition when neuropathy of a subject is treated, and relieves work difficulty of medical staff.

WO 2005098726 A2 discloses a device that includes not only a client program that runs on a computer with a standard operational system but also a portable device (hardware) and embedded software for analog digital conversion of electrical signals and mechanical values (blood pressure). This reference enables measurement of the electrical signals and mechanical values of the subject such as ECG/EEG/Blood pressure which are controlled by appropriate hardware and the embedded program. Video information of the subject in a real time is generated by standard system for video conferencing. The standard system for video conferencing on the subject's side establishes communication with the standard system for video conferencing at specialist medical doctor practice after commutation of communication channels enabled by web-agent at the host computer. Precisely, invention is about portable ECG EEG device, standard digital blood pressure and standard system for video conferencing that can be controlled from a remote personal computer, PDA, cell phone or similar device that runs client program or equivalent of client program and communicates with server program through the Internet or other type of public or private network.

None of the above related prior art discloses the tracking (monitoring) of subject without the intervention of a technologist or caregiver. During a seizure attack, there is every possibility of the subject going out of focus of the camera, due to the natural movement as well as involuntary movement or falls during seizures. It can then only be refocused by the technologist or a caregiver. Additionally, the prior art does not provide for a simultaneous focus on any specific part(s) or multiple parts(s) of the subject's body during a seizure episode. Moreover, the prior art does not disclose detecting an obstruction between the subject and the camera.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An object is to provide a lightweight, simple and a fully automated portable Video EEG device for seizure diagnosis.

Another object is to make the process of video recording fully automatic and complete the recording without any intervention from the caregiver or technologist.

Another object is to automatically track, focus and record the subject's movement without any intervention from the technologist or a caregiver.

A further object is to obviate the need for manually activating an event button for marking the start and/or end of seizure activity.

Another object is to ensure synchronization of the camera and EEG for precision.

A further object is to automatically detect any obstruction between the subject and the camera.

A further object is to automatically warn if the subject is too far away or too near from the camera.

A further object is for the telescoping stand with the camera to automatically follow and record the subject in a multi-room scenario.

A further object is to provide for a mechanism to focus on various aspects of the subject's body simultaneously during a seizure episode by using multiple zoom function as a part of integrated subject friendly display software.

A further object is to present the seizure data (both video and EEG) immediately to the neurologist. Immediate access to seizure data results in faster diagnosis.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments relate to a system and method for seizure diagnosis by Video Electroencephalography (Video-EEG). More particularly, the invention relates to a fully automated method and apparatus for monitoring subjects suffering from seizure in order to receive a diagnosis. Various embodiments may also be used by healthcare facilities or other point of care facilities to conduct video monitoring.

Embodiments described herein provide an efficient video EEG apparatus which is a fully automated system designed to monitor the subject without any intervention from the EEG technologist or a caregiver. The integrated system can receive and record EEG signals while the video for the procedure is recorded by the integrated camera in a synchronized manner. The camera is capable of recording at high resolution (at least 4K at high frame rates) wherein the recorded video is stored either locally or streamed and stored on a remote server.

Various embodiments generally relate to a fully automated system for diagnosis of seizures. The integrated system can simultaneously receive and record EEG signals while the video for the procedure is recorded by the integrated camera and is designed to work without any intervention from an EEG technologist or a caregiver. Various embodiments also relate to a method and apparatus for monitoring subjects suffering from seizure in order to receive a diagnosis.

Figure 1:
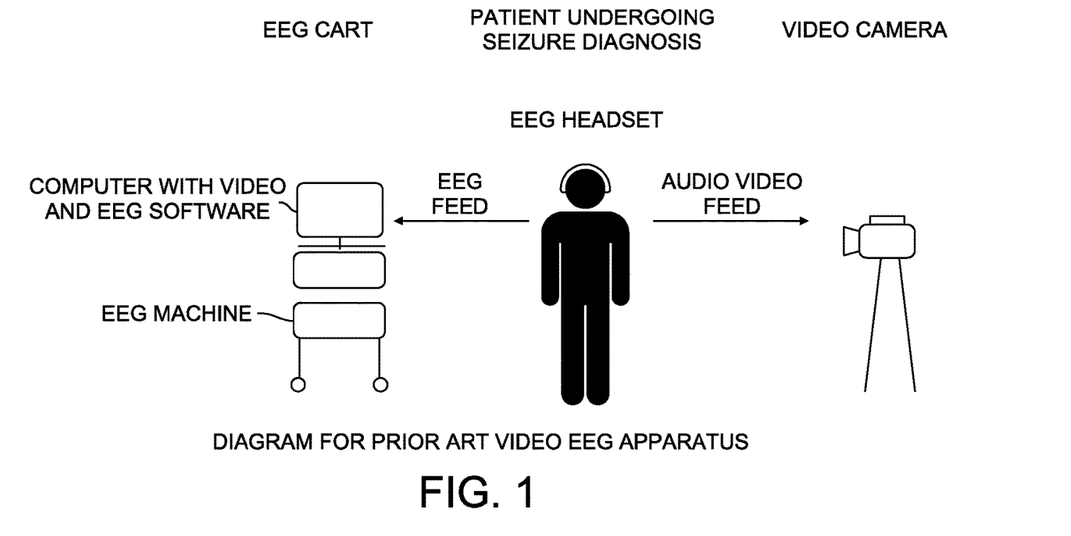
FIG. 1 is a block diagram of a prior art version of a video EEG apparatus.

FIG. 1 is a block diagram of a prior art of video EEG apparatus. It's a conventional apparatus which includes a video camera and an EEG setup comprising of EEG headset, and the EEG recorder that feeds information to a personal computer having EEG and video software.

Figure 2:
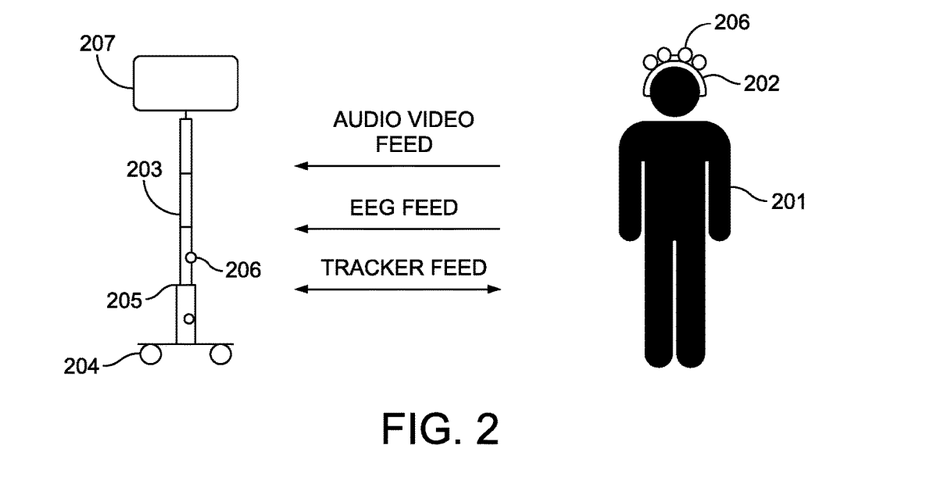
FIG. 2 is a block diagram of an exemplary embodiment of a video EEG apparatus.

FIG. 2 is a block diagram of an embodiment of a video EEG apparatus. Various embodiments relate to a device comprising of hardware and software components:

A. A tracker cap 202 (Henceforth referred to as "tracker") which may optionally be worn on the subject's 201 head or can be worn on other body part.

B. A swiveling stand (henceforth referred to as "stand") 203: The stand has motors for rotation along multiple axes. The aforementioned stand will have a base with wheels 204 for motion. The wheels would be driven by various motors. The aforementioned stand will be telescoped 205 to accommodate for various heights of subjects and will have various sensors 206 to facilitate rotation along various axes such as Ultrasonic, Infrared sensors, radio transceivers and so on. The stand will have hinge and mechanism for connection and placement of tablet computer 207.

C. A tablet computer like device 207 with various ports but not limited to Ethernet, USB etc. wherein the tablet computer has in built front facing and back facing cameras or multiple cameras in front and back. The said tablet computer 207 could optionally be connected to the swiveling stand 203 via standard ports like USB, Firewire, or any other mechanism. The said swiveling stand along with the said tablet computer and will act as a single unit and henceforth be referred to as the 'stand'.

D. Mobile tablet Operating System (OS) software.

E. Camera application software.

F. EEG software.

G. Motion detection/patient tracking/patient monitoring software.
H. Obstruction detection software.
I. Seizure detection and event tagging software.
J. Device software—Tracker.
K. Device software—Stand.
L. Communication software.
M. Notification software.

Sensors 206 are present on the tracker 202 and the stand 203 for the purposes of tracking motion of the subject and communication with each other. The tracker is integrated with the EEG device or could optionally be attached to commercially available EEG devices to record video synchronized to the EEG tracing.

The tracker 202 communicates with the unified tablet and stand system referred to as stand 203 to send EEG signals as well as sends tracking information of the subject. Thus, there is two-way communication between the camera module and EEG software.

Figure 3:
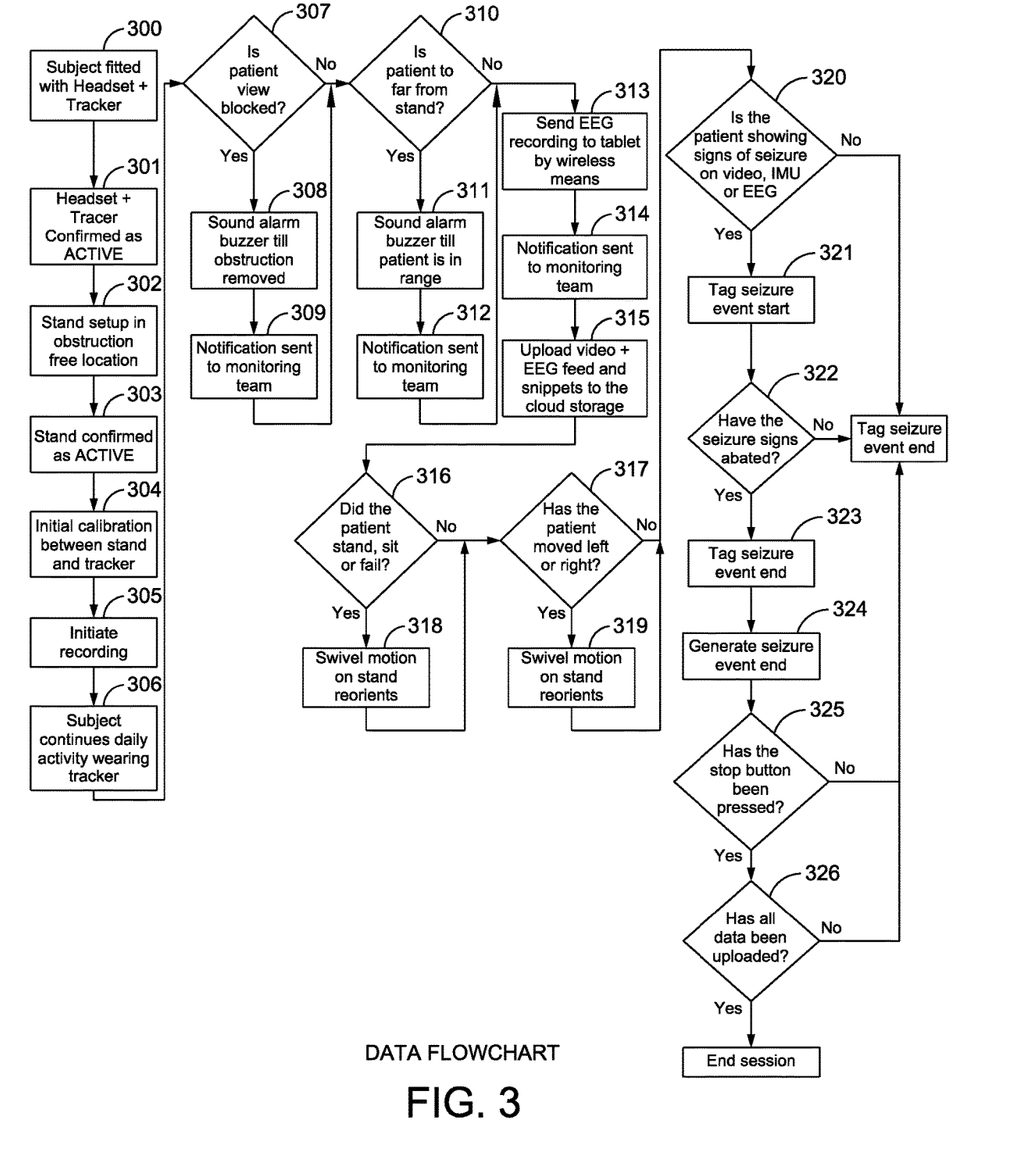
FIG. 3 is a flowchart depicting an entire procedure of an exemplary embodiment.

FIG. 3 depicts the entire procedure of tracking the subject in form of a flow chart. The following steps illustrate the happenings during a typical session. The procedure begins once the subject is fitted with headset and tracker (step 300). The headset and tracker is confirmed active (step 301) and the stand is setup in an obstruction free location (step 302). Now the stand may be also confirmed as active (step 303). An initial calibration between the stand and tracker is done (step 304) and the recording is initiated (step 305). EEG recording data is received from the person via any wired or wireless mechanism. As the data is received, a baseline EEG recording is established. This baseline is the normal (seizure free) reading. An elevated signal means a spike in EEG, and a baseline refers to the regular reading of EEG. The subject continues daily activity wearing a tracker (step 306). A determination is made whether the subject view is blocked (step 307). If there is an unwanted obstruction, an alarm is sounded off to remove the obstruction (step 308) and a notification is sent to the monitoring team (step 309). It is further determined whether the subject is standing too far from the stand (step 310). A buzzer is sounded off if the subject is out of range (311) and simultaneously, a notification is sent to monitoring team (step 312). EEG recording is sent to the tablet by wireless means (step 313). (Note that this data can be sent by wired means if necessary.) A notification is sent to team (step 314) and the video and EEG feed and snippets are uploaded to the cloud storage (step 315). A determination is also made, whether the subject is standing, sitting or fell down (step 316) or has moved left or right (step 317), the stand reorients itself (steps 318, 319). If the subject shows signs of seizure on video, IMU or EEG (step 320), seizure event tagging is initiated (step 321). Once the seizure signs are abated (step 322), i.e., IMU sensor defaults back to regular reading, seizure event tagging ends (step 323) and the seizure event snippet is generated (step 324) and the video data and the EEG data for the tagged period is now packaged as an event and uploaded to the server immediately to be made available to the neurologist.

A stop button is pressed to stop recording process (step 325). Once all the video and EEG data has been uploaded (step 326), the procedure is stopped. This video and EEG data is made available to the neurologist for diagnosis. The entire mechanism of seizure event detection and the movements of subject are described in detail henceforth.

SEIZURE EVENT DETECTION AND TAGGING MECHANISM—Various embodiments relate to the ability to accurately capture normal as well seizure episodes of the subject during the session. There are multiple ways seizure events are automatically tagged and recorded by various embodiments. When seizure occurs, the tablet system automatically tags the event via a combination of motion detection algorithm, signals received from the tracker, video image analysis and/or detection of elevated signals from the EEG headset.

A number of specific types of sensors that are used in different embodiments are described herein for the seizure event detection. This description of sensors is not intended to be limiting since many other types of sensors that may be used in lieu of or in addition to those specifically described will be apparent to those of skill in the art. Below list of sensors, their location and their functionality are described for better understanding:

Ultrasound (US) sensors may include transmitter and receiver units. These may be located on the stand. The function may include capture of vertical movement of the subject such as standing up, sitting down or falling down. It also captures the movement of the subject towards (approaching) or away (receding) from the stand.

In an exemplary process, the US transmitters on the stand emit ultrasonic waves. The US receivers on the stand then receive these waves. Based on the time taken for the waves to reach the US receivers, the distance between the stand and subject is calculated. If there is a change in the vertical location (subject moving up/down), the software instructs the tablet swivel mechanism to reorient up/down to the new location of the subject. If there is a change in the distance from the stand (subject coming near/going far) then the software instructs the stand locomotion mechanism to follow the subject. If the waves go out but are not received back, this indicates that the subject has left the building or moved out of the sensor range.

Infrared (IR) sensors may include transmitter and receiver units. These may be located on the stand. The tracker has the IR receiver(s) placed in a ring like orientation. FIG. 2 shows the tracker worn on the subject's head. In an embodiment, the function is capturing the lateral movement of the subject i.e., if the subject moves left or right with respect to the stand. They also capture any obstructions blocking the view between the subject and the stand. An exemplary process may include infrared waves sent by the IR transmitters on the stand. The IR receivers on the tracker receive these waves. Only the IR receivers in direct line or within their angle of reception of the IR transmitters will receive the waves successfully. The remaining IR receivers will show no wave reception. If the subject moves laterally, say to the left, the IR receivers on only one side will receive the waves. Based on this, the software instructs the swivel mechanism to reorient left towards the new location of the subject. If say another person blocks the path between the stand and the subject, then none of the IR receivers will receive any wave. The software then identifies this as an obstruction.

Inertial motion unit (IMU) sensors may include accelerometer, gyroscope and compass sensor components. The location may be with the tracker having the inertial motion unit sensors on it. Additionally, the stand may include its own IMU sensor unit. The function may include three sub-assembly components of an inertial motion unit sensor: the 'accelerometer' provides an estimate of the velocity of the subject, the 'gyroscope' measures rotation along the axis and, the 'compass' measures orientation with respect to the magnetic north-south. It captures the rotation of the subject's head. It also captures any jittery motion of the subject indicative of a seizure in progress.

In an exemplary embodiment, the process may include a routine when the subject turns his or her head rightwards or leftwards, the gyroscope and the compass provide a measure of the rotation. If there is excessive motion of the head (termed jittery motion), the system processes this information as indication of a seizure and proceeds to seizure event tagging.

One or more radio transceivers may be located on the tracker. The stand has its own transceiver unit. The functions of transceivers include the capability of both, sending and receiving radio waves and enable two-way communications between the tracker and the stand.

Figure 4:
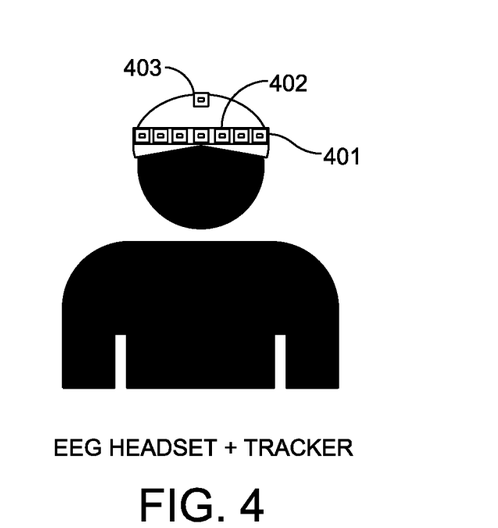
FIG. 4 is a schematic representation of a tracker in accordance with various embodiments.

FIG. 4 illustrates a wearable tracker 401. The implementation shows the tracker worn on the head of the subject. The tracker various embodiments may include a ring like structure worn by the person on the head. The tracker could be a part of an integrated EEG headset or worn on top of an EEG headset. The tracker may include of plurality of sensor units 402. FIG. 4 shows implementation with (infrared) IR receivers placed along the circumference of the ring. This is used for motion tracking relative to the stand 203. It further shows an implementation that includes an Inertial Motion Unit (IMU) sensor (403) that is used to track any jittery motion by the subject indicating a possible seizure. It may also be used for purposes of head tracking of the subject. The implementation may also include radio sensors for communicating with the stand.

Figure 5:
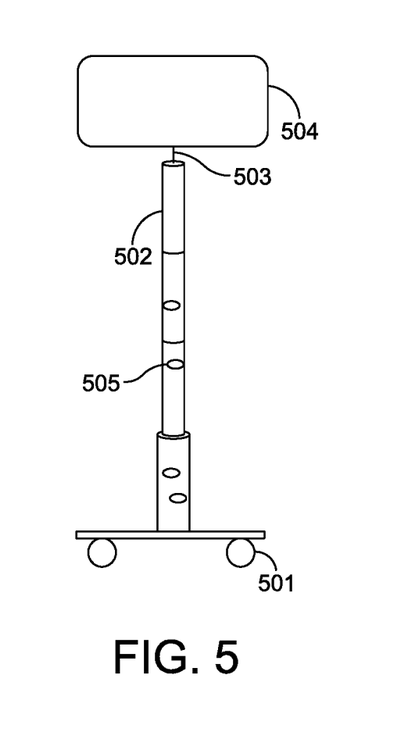
FIG. 5 is the schematic representation of the telescoping stand exhibiting a strip of infra-red and ultrasonic emitters arranged in plurality on the telescoping stand in accordance with an embodiment.

FIG. 5 is a more detailed diagram of the stand. The stand may be portable and movable, and may include the following components:

A base with wheels for locomotion 501.

A telescoping mechanism 502.

A swivel mechanism 503. The swivel mechanism consists of various motors and is capable of rotation along various axes to facilitate tracking of subject. For instance, it can rotate 360 degrees along vertical axis and 180 degrees along horizontal axis.

A mobile computing device such as a tablet 504 that is connected via hinge to the swivel mechanism. This allows the camera in the tablet to track the subject. The mobile tablet hinge can also house a computer connection mechanism such as, but not limited to USB or Firewire et al. This allows the tablet to receive data from various sensors. It is also used to send any data.

A vertical array of sensors 505. The said sensors may either be of one type or a combination of sensors. FIG. 5 shows implementation with Ultrasonic (US) and Infrared sensors. The Ultrasonic sensors may include an emitter and a receiver. For example, the infrared sensors are emitters. This vertical array is also connected to the swivel mechanism thus allowing it to track the subject.

MOTION DETECTION AND TRACKING MECHANISM—If the subject moves, the camera tracks the subject to maintain focus. This is accomplished by data received from the tracker. In case the subject moves outside of predefined distance or to another room, the stand transports itself and follows the subject. The obstruction detection mechanism recognizes an obstruction of view of the subject from the camera and signals an alarm.

The tracker can help track various movements of the subject including movements such as sideways movement with respect to the stand.

Figure 6A:
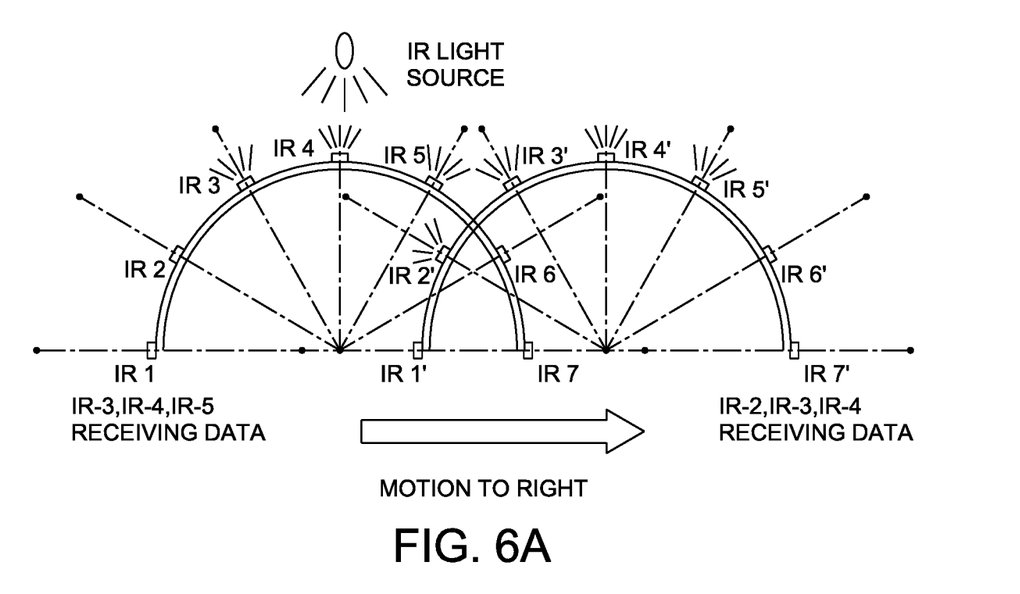
FIG. 6A shows the tracking of horizontal motion of the subject from left to right in accordance with various embodiments.
Figure 6B:
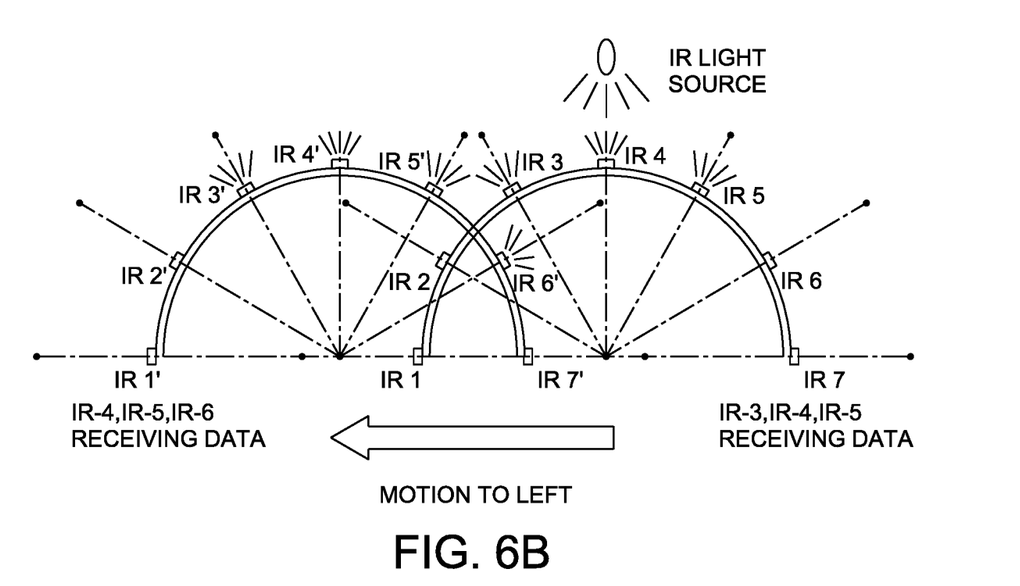
FIG. 6B shows the tracking of horizontal motion of the subject from right to left in accordance with various embodiments.

SIDEWAYS MOTION TRACKING MECHANISM—Illustratively, FIGS. 6A and 6B depict the process of tracking horizontal motion (left or right) with built in sensors. FIGS. 6A and 6B shows sensors implemented with IR emitters and IR receivers. The sideways motion tracking is achieved by sensing IR radiation. The algorithm is based on the "rightmost" or "leftmost" sensor receiving light as illustrated below.

In FIG. 6A, the process of tracking the subject, when subject moves right is shown. By way of representation, the tracker is shown as a semicircle for convenience. Though there is plurality of IR receivers, by way of illustration, only six are shown. The FIG. 6A shows what happens when the person moves right. The tracker, at first is receiving IR light (from the IR emitters from the sensor array on the stand). Right now, only IR3, IR4 and IR5 (these are infrared receivers) are receiving them. When the person moves right, IR5 does not receive the light anymore. Now, IR2, IR3 and IR4 are receiving. IR2 is now the "leftmost" sensor receiving light. That implies the person "moved right".

Similarly, if the person moved left is depicted in FIG. 6B. The tracker at first is receiving IR light (from the IR emitters from the sensor array on the stand). Right now, only IR3, IR4 and IR5 (These are Infrared receivers) are receiving them. When the person moves left, IR4, IR5 and IR6 are receiving. IR6 is now the "rightmost" sensor receiving light. That implies the person "moved left".

MECHANISM FOR TRACKING VERTICAL MOTION SUCH AS STANDING UP, SITTING DOWN AND FALLING—When a person sits down or stands up, the tracking of the motion is accomplished using ultrasonic sensors located on the stand. Ultrasonic sensors operate on obstruction. An ultrasonic sensor has a sound emitter and a receiver. The emitter sends a sound wave. Once the sound wave hits a barrier, it returns back and is received by the receiver. Using the speed of sound and the time it took for a sound wave to get back to the receiver, one can find the distance between the sensor and a barrier.

Figure 7A:
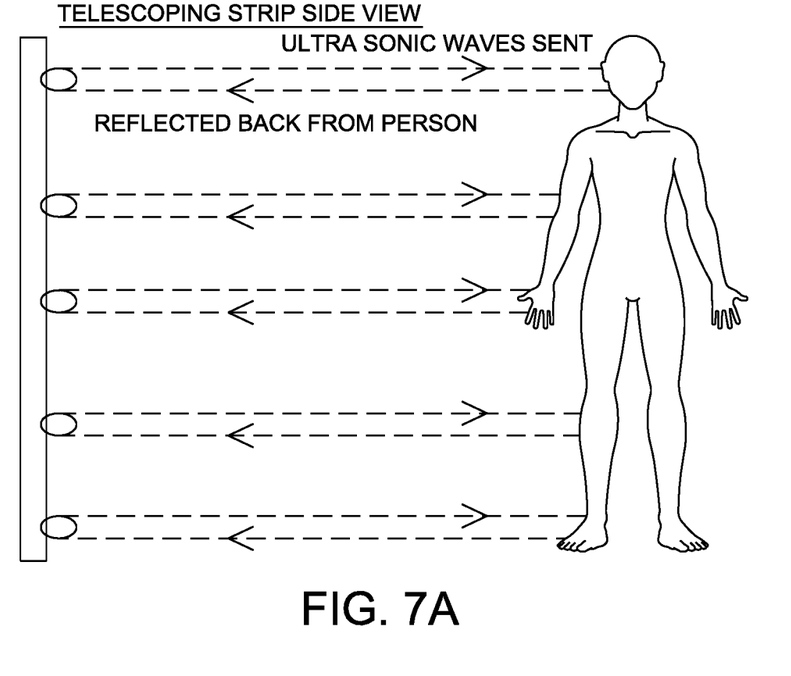
FIG. 7A shows the tracking of the subject when he/she is standing in accordance with various embodiments.
Figure 7B:
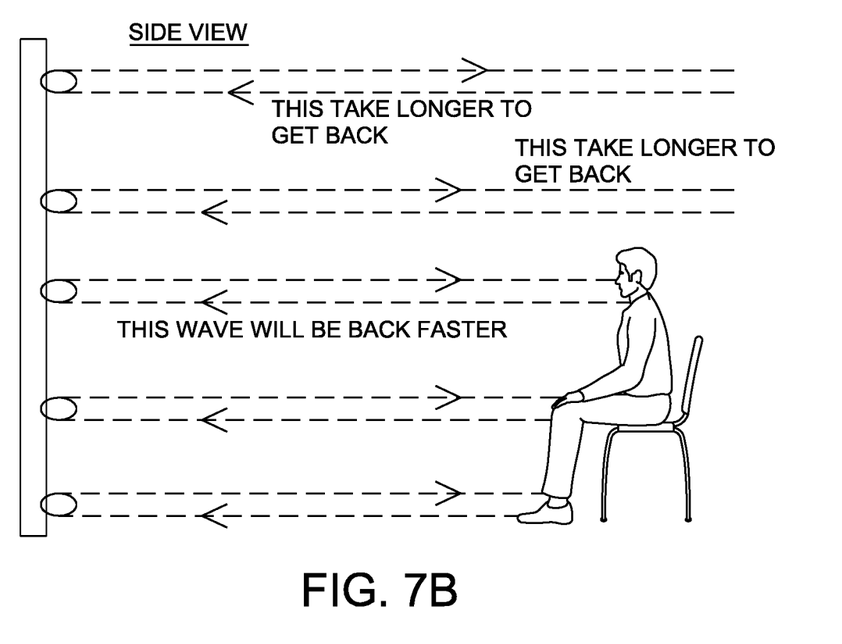
FIG. 7B shows the tracking of the subject when he/she is in sitting or prone position in accordance with various embodiments.

FIGS. 7A and 7B depict vertical movements of the subject. As shown in FIG. 7A, the subject is standing in front of the stand which has both IR and US sensors. For vertical movements ultrasonic sensors come in to play. For illustration purpose, 5 Ultrasonic sensors are shown in FIGS. 7A and 7B. These sensors send out the sound waves, which hit the subject and returns back. The time taken by sound waves to return back is same, but when the subject is sitting as depicted in FIG. 7B, the top two ultrasonic receivers take more time to return compared to the bottom sensors as the bottom sensors hits the subject and returns back. Using these time calculations, one can deduce that the person is "vertically down".

MECHANISM FOR TRACKING THE SUBJECT WHEN APPROACHING OR RECEDING FROM THE STAND

Figure 8:
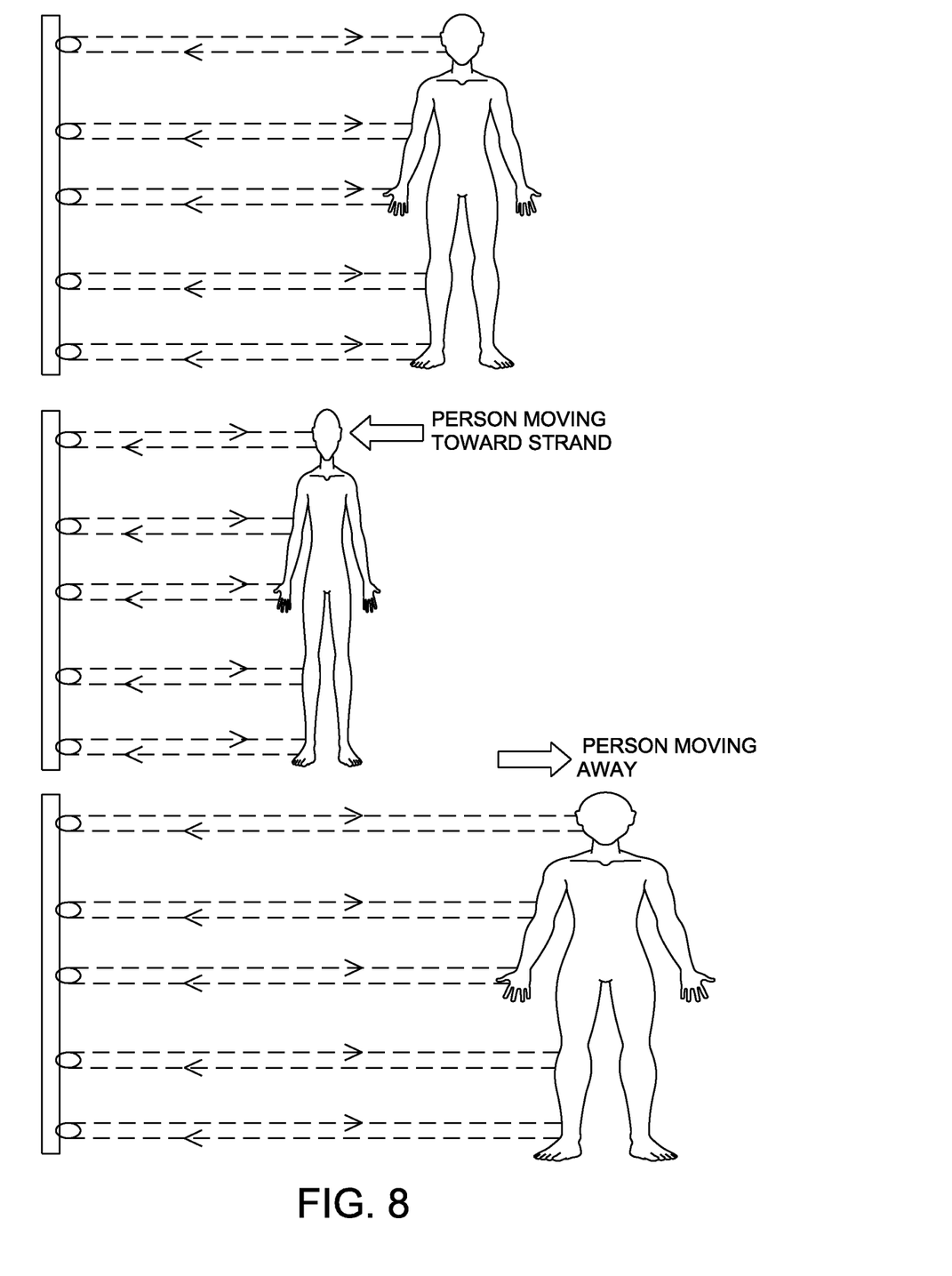
FIG. 8 shows the tracking of the subject when he/she is approaching or receding from the stand in accordance with various embodiments.

FIG. 8 shows that when a subject approaches or recedes from the stand, the tracking of the motion is accomplished using Ultrasonic sensors located on the stand. Ultrasonic sensors operate on obstruction. A sensor has a sound emitter and a receiver. The emitter sends a sound. After sound wave hits a subject, it returns and is received by the receiver. Using the speed of sound and the time it took for sound to get back to the receiver, one can find the distance between the sensor and a subject. Based on the calculated change in distance the stand can move to follow the subject to maintain a viable camera recording and tracking distance.

Figure 9:
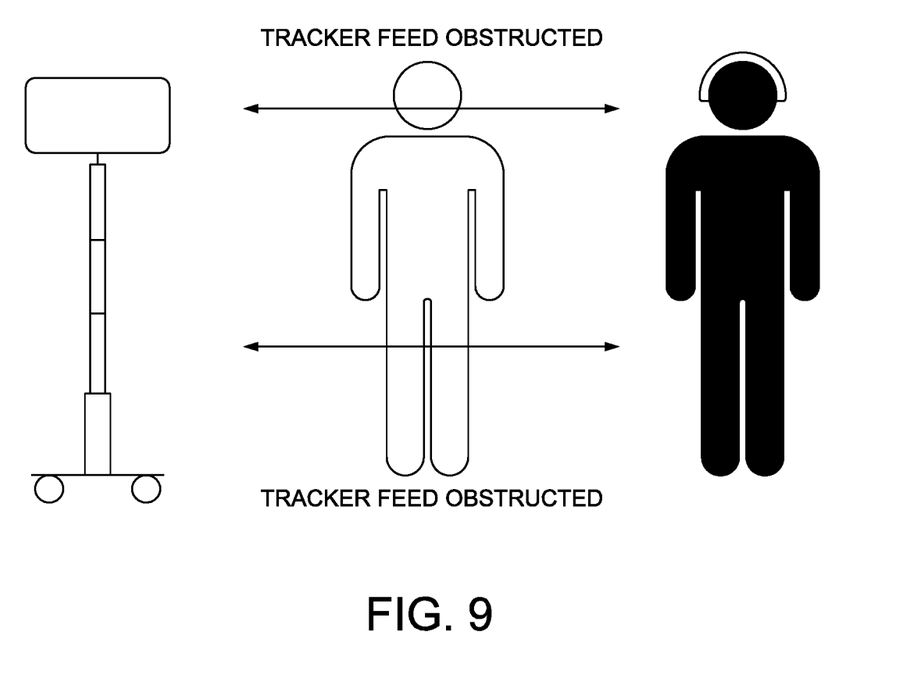
FIG. 9 illustrates obstruction detection mechanism in accordance with various embodiments.

OBSTRUCTION DETECTION MECHANISM—Obstruction detection is one of the important aspects of various embodiments as illustrated in FIG. 9. When a person (like a caretaker/nurse or a relative) or an object comes in between the subject and the camera, it blocks the view of the subject on camera. If the person experiences seizure during this process, valuable recording will be lost. Hence it is important to warn of the obstruction and to clear it. The infrared sensor array is used to perform obstruction detection. Obstruction is detected via lack of reception of IR signal to the tracker that is on the head of the subject in this implementation. When there is no obstruction, at least one or more receivers in the tracker receives IR signal. In the event of obstruction, none of the IR receivers receive an IR signal which results in the sounding of the alarm.

MULTIPLE ZOOM MECHANISM—This aspect of the invention is related to the post processing and viewing of seizure event by neurologists. Neurologists benefit from looking at all aspects of the subject during a seizure. Movement of the limbs, eyes, head, and orientation of the body are some of the things that neurologists would utilize to come up with a differential diagnosis of a seizure. To facilitate this requirement, the apparatus of various embodiments may be integrated with multipoint zoom software which is designed to give multiple and simultaneous (via split screen) views of seizure episodes (events) to the neurologist. This further provides various image processing features to aid the neurologist in the diagnosis of seizures. Multi point zoom offers to zoom the video from any point in the video frame. This feature allows the observer to focus and zoom on any specific area in the video.

Figure 10:
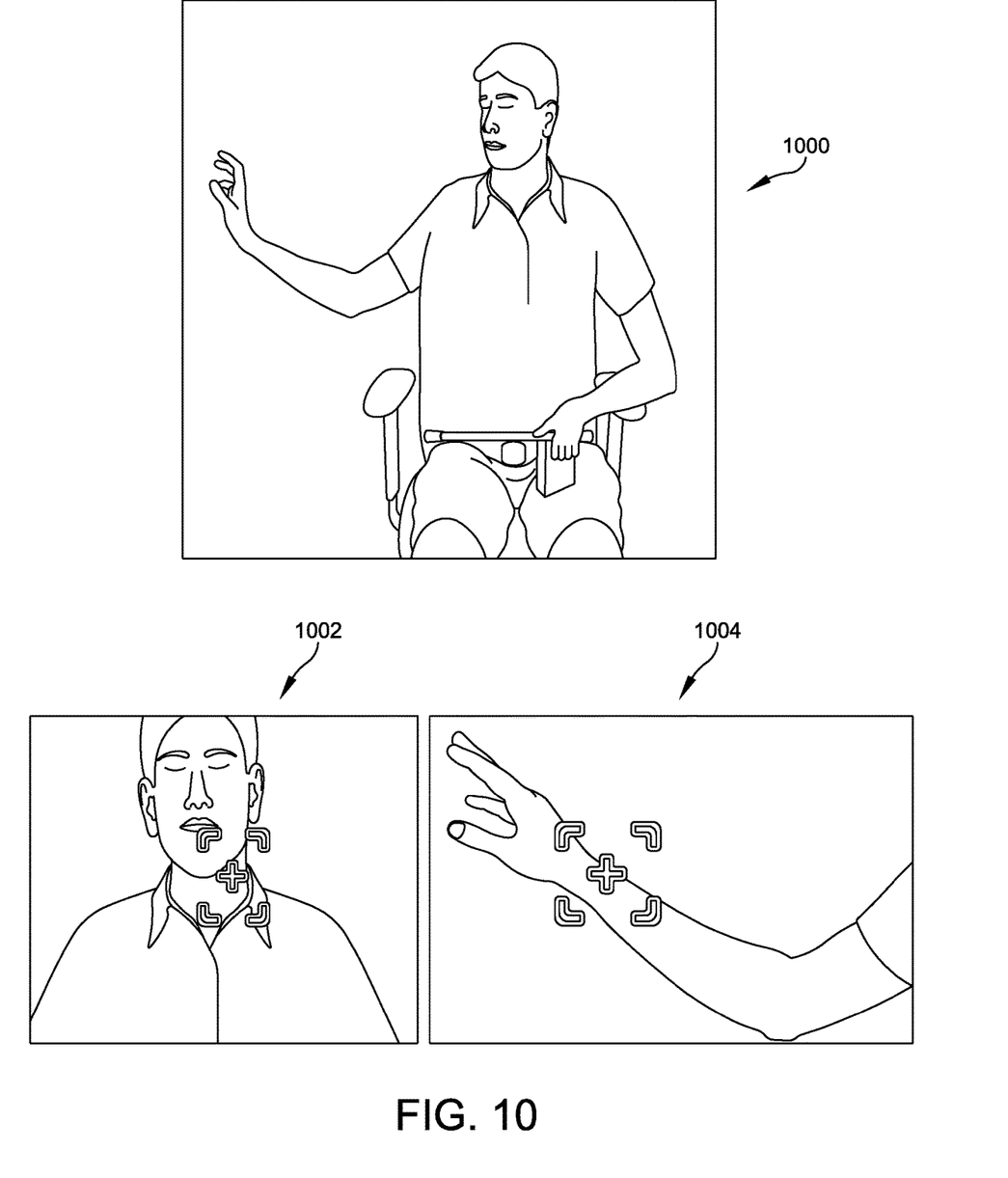
FIG. 10 illustrates the multipoint zoom feature in accordance with various embodiments depicting a split view showing the video zoomed on the hand and the head.

To illustrate, as shown in FIG. 10, if an observer wishes to zoom and focus on the head and hand. The video 1000 splits to two views with the head zoomed in on the left video 1002 and the right video 1004 can be focused on hand which can be zoomed in. In conventional video software, the subject can zoom in or zoom out a video for closer look and analysis. However, the video frame always zooms in from the center of the video frame. If our object/area of interest is not at the center, or near the center, zooming in might render the area of interest outside of the video frame. In this case, zoom is not helpful to us. For example, during seizure event, if the neurologist wants to zoom in on the head and if the head is not near the center of the video frame, zooming in will render the head outside of the frame. To overcome this drawback, the invention focuses on "multi point zoom". With this mechanism, any area in the video frame can become "center". The neurologist can now designate head as the "center" of the frame. When he/she now zooms in, the head will now come into focus. The neurologist now gets a magnified view of the area of interest.

COMMUNICATION MECHANISM—Another aspect of various embodiments may be that a notification (like via alarm or mobile message) is sent to the technologists or the caregiver when seizure starts. This automated notification is used by the technologist or a caregiver to give immediate attention to the subject.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A fully automated, portable, point-of-care diagnostic video EEG system, the system comprising:
   a tracker configured for placement on a patient, the tracker having a set of sensors disposed thereon;
   an EEG headset configured for detecting electrical activities of a brain of the patient, and the EEG headset configured for communicating the electrical activities of the brain of the patient; and
   a telescoping stand with built-in sensors, a mobile computing device in communication with the built-in sensors and in communication with the EEG headset, and a set of wheels for controlled movement of the telescoping stand.

2. The system of claim 1, wherein the tracker further comprises at least one of an internal motion unit (IMU) sensor, a radio sensor and plurality of IR receivers for communicating with telescoping stand.

3. The system of claim 1, wherein the telescoping stand includes at least one of a plurality of IR and ultra sound (US) sensors for analyzing movements of the patient in any direction and radio transceivers for communication.

4. The system of claim 3, wherein the telescoping stand is configured to automatically track and move to follow the patient when the patient moves from one place to another.

5. The system of claim 1, wherein the mobile computing device further comprises custom written software such as camera application software, EEG software, motion detection/subject tracking/subject monitoring software, obstruction detection software, seizure detection and event tagging software, device software for tracker and stand, communication software, and notification software[, and android or other operating system, APIs (Application programming interface)].

6. The system of claim 1, wherein the tracker is a cap configured for placement on the patient, and the set of sensors is disposed on the cap.

7. The system of claim 6, wherein the tracker is configured for disposal over the EEG headset.

8. The system of claim 1, wherein the tracker and the EEG headset are integrated with one another.

* * * * *